United States Patent
Goren et al.

(10) Patent No.: US 10,111,821 B2
(45) Date of Patent: Oct. 30, 2018

(54) METHODS AND COMPOSITIONS FOR ADMINISTERING A SPECIFIC WAVELENGTH PHOTOTHERAPY

(71) Applicant: Follea International, Irvine, CA (US)

(72) Inventors: Andy Ofer Goren, Newport Beach, CA (US); John McCoy, Downey, CA (US)

(73) Assignee: Applied Biology, Inc., Irvine, CA (US)

( * ) Notice: Subject to any disclaimer, the term of this patent is extended or adjusted under 35 U.S.C. 154(b) by 0 days.

(21) Appl. No.: 14/145,824

(22) Filed: Dec. 31, 2013

(65) Prior Publication Data

US 2014/0121732 A1 May 1, 2014

Related U.S. Application Data

(63) Continuation-in-part of application No. 13/948,090, filed on Jul. 22, 2013, which is a continuation-in-part of application No. 13/669,435, filed on Nov. 5, 2012.

(60) Provisional application No. 61/555,130, filed on Nov. 3, 2011.

(51) Int. Cl.
*A61K 8/60* (2006.01)
*A61K 31/7048* (2006.01)
*A61K 31/216* (2006.01)
*A61K 31/12* (2006.01)
*A61K 31/357* (2006.01)
*A61K 31/24* (2006.01)
*A61N 5/06* (2006.01)
*A61Q 17/04* (2006.01)
*A61Q 5/00* (2006.01)

(52) U.S. Cl.
CPC .............. *A61K 8/602* (2013.01); *A61K 31/12* (2013.01); *A61K 31/216* (2013.01); *A61K 31/24* (2013.01); *A61K 31/357* (2013.01); *A61K 31/7048* (2013.01); *A61N 5/0613* (2013.01); *A61N 5/0616* (2013.01); *A61Q 5/00* (2013.01); *A61Q 17/04* (2013.01); *A61K 2800/81* (2013.01); *A61N 2005/0628* (2013.01); *A61N 2005/0655* (2013.01); *A61N 2005/0657* (2013.01); *A61N 2005/0661* (2013.01); *A61N 2005/0667* (2013.01)

(58) Field of Classification Search
None
See application file for complete search history.

(56) References Cited

U.S. PATENT DOCUMENTS

| | | | |
|---|---|---|---|
| 5,300,097 A | 4/1994 | Lerner et al. | |
| 5,573,753 A | 11/1996 | Tapley | |
| 5,747,010 A | 5/1998 | Geesin et al. | |
| 6,130,435 A | 10/2000 | Rocklin | |
| 6,423,747 B1 | 7/2002 | Lanzerdorfer et al. | |
| 6,716,996 B1 | 4/2004 | Srinivasan et al. | |
| 2007/0085063 A1 | 4/2007 | Capelli | |
| 2010/0021400 A1 | 1/2010 | Jay et al. | |
| 2010/0226861 A1 | 9/2010 | Cole et al. | |
| 2012/0288478 A1* | 11/2012 | Florence | A61K 8/64 424/93.1 |

FOREIGN PATENT DOCUMENTS

| | | | | |
|---|---|---|---|---|
| JP | 61-167613 A | 7/1986 | | |
| JP | 2006-523593 A | 10/2006 | | |
| KR | 1995-0012443 B1 | 10/1995 | | |
| WO | WO-2006020165 A1 * | 2/2006 | | A61K 8/498 |

OTHER PUBLICATIONS

Peterson et al., Journal of Food Composition and Analysis; vol. 19 (2006), S74-S80.*
Vina et al.; J. Braz. Chem. Soc.; vol. 14, No. 5, 744-749 (2003).*
Sass & Veracity website for Grapefruit, Avocado, and Basil salad (sassandveracity.com/2011/02/25/grapefruit-and-avocado-salad-with-basil/); published Feb. 25, 2011; downloaded Dec. 15, 2016.*
International Search Report and Written Opinion for PCT Applicaton No. PCT/US13/51721 dated Dec. 20, 2013.
PCT International Search Report and Written Opinion in International Application No. PCT/US2012/063628, dated Nov. 5, 2012.
Office Action (Restriction) in U.S. Appl. No. 13/948,090, dated Dec. 24, 2104.
Wallengren et al. "Cutaneous Field Stimulation in the Treatment of Severe Itch", Arch. Dermatol. vol. 137, No. 10, Oct. 2001, pp. 1323-1325.

* cited by examiner

*Primary Examiner* — Jeffrey T. Palenik
(74) *Attorney, Agent, or Firm* — Buchanan Ingersoll & Rooney PC

(57) ABSTRACT

Methods are disclosed for administering electromagnetic radiation (EMR), which may include filtering EMR from part of the EMR spectrum while allowing passage of EMR at a desired wavelength range. Uses may include the treatment of such conditions as psoriasis, vitiligo, pruritus, acne, vitamin-D deficiency and atopic dermatitis. Topical creams, sprays, or other compositions may be used, with or without dosimeters, or in conjunction with an application, which calculates local UV exposure and other factors relating to dosage.

14 Claims, 12 Drawing Sheets

PHOTOCREAM DOSIMETER APLIQUE STICKER

250 mJ Dosage Indicator 500 mJ Dosage Indicator

METHODS AND COMPOSITIONS FOR ADMINISTERING A SPECIFIC WAVELENGTH PHOTOTHERAPY

CROSS-REFERENCE TO RELATED APPLICATIONS

This application is continuation-in-part of U.S. application Ser. No. 13/948,090, filed Jul. 22, 2013, entitled "Methods and Compositions for Administering a Specific Wavelength Phototherapy," which is a continuation-in-part of U.S. application Ser. No. 13/669,435, filed Nov. 5, 2012, entitled "Methods and Compositions for Administering a Specific Wavelength Phototherapy," which claims priority to U.S. Provisional Application No. 61/555,130, filed Nov. 3, 2011, entitled "System and Method for Administering a Specific Wavelength Phototherapy," all of which are incorporated herein in their entirety.

BACKGROUND

Technical Field

The inventions described herein relate to methods and compositions for administering electromagnetic radiation (EMR), for therapeutic or cosmetic purposes.

Description of the Related Art

Many dermatological conditions, such as psoriasis, vitiligo, atopic dermatitis, acne and pruritis show a strong response to phototherapy. Narrowband-UVB (NB-UVB), a UV phototherapy that utilizes a 308 nm or 311 nm wavelength, or thereabouts, has been shown to be a safe and effective modality for UV phototherapy. Similarly, blue light therapy in the visible range has been shown to be clinically effective for the treatment of acne. Currently, most effective phototherapy is administered in medical offices.

While effective, compliance with NB-UVB phototherapy is low due to the time commitment required for the treatment. For example, psoriasis patients undergoing NB-UVB phototherapy need to visit a specialized medical clinic two to three times a week for a period of three months. This significant time commitment is the main drawback of phototherapy and results in low compliance. In addition, high co-pays and a declining number of centers offering phototherapy make access limited. Therefore, a phototherapy alternative that patients can safely and cost-effectively use at their convenience would be beneficial.

Portable phototherapy lamps are available for in home use; however, applying proper and effective dosage may be difficult and unsafe for patients. In addition, when phototherapy is administered at medical offices, an artificial light source (NB-UVB) is used. The light source emits NB-UVB at a specific therapeutic range as well as a significant amount of non-therapeutic harmful UVB. A topical agent that can reduce harmful radiation exposure from phototherapy lamps would also be highly valuable for patient safety.

BRIEF SUMMARY

Described herein are methods for administering specific wavelengths of electromagnetic radiation while excluding electromagnetic radiation of other frequencies. Such methods may be used for treatment of psoriasis, vitiligo, atopic dermatitis, eczema, acne, pruritus, and other therapeutic or cosmetic purposes.

One embodiment described herein is a topical composition comprising: a cosmetic-grade carrier suitable for application to human skin; and a compound, suitable for application to human skin, which may block substantially more UVB light at wavelengths below about 310 nm than at wavelengths above about 310 nm. This compound may be, for example, hesperidin or a cinnamate, such as methyl cinnamate. In another embodiment of the above, the composition may further comprise a second compound, suitable for application to human skin, which may block substantially more UVA or UVB light at wavelengths above about 310 nm than at wavelengths below about 310 nm.

In another embodiment, in addition to the cosmetic-grade carrier suitable for application to human skin, the composition may include a compound, suitable for application to human skin, which blocks more total radiation within wavelength range B (280 to 300 nm) than it blocks in wavelength range A (300 to 320 nm). In this example, the topical composition may blocks a percentage $PF_B$ of radiation in wavelength range B that is greater than a percentage $PE_A$ of radiation blocked in wavelength range A, wherein $PE_A$ is defined as:

$$PF_A = 1 - \frac{\int_{300\,nm}^{320\,nm} I(\lambda) \cdot w(\lambda) \cdot T(\lambda) d\lambda}{\int_{300\,nm}^{320\,nm} I(\lambda) \cdot w(\lambda) d\lambda}$$

and wherein $PF_B$ is defined as:

$$PF_B = 1 - \frac{\int_{280\,nm}^{300\,nm} I(\lambda) \cdot w(\lambda) \cdot T(\lambda) d\lambda}{\int_{280\,nm}^{300\,nm} I(\lambda) \cdot w(\lambda) d\lambda}$$

where $\lambda$ is a wavelength of radiation, $I(\lambda)$ is an intensity of radiation according to solar irradiance standard ASTM G177-03 passing through the topical composition at a given wavelength in $W/m^2/nm$, $T(\lambda)$ is the mean transmittance of a topical composition determined using the methodology outline in the US FDA Broad Spectrum Test (21 CFR 201.327(j), Jul. 5, 2011), and $w(\lambda)$ is a weighting function defined as:

$$w(\lambda) = \begin{cases} 1 & 280\,nm < \lambda \leq 298\,nm \\ 10^{0.094(298-\lambda)} & 298\,nm < \lambda \leq 320\,nm \end{cases}$$

wherein $PF_B-PE_A$ is some percentage such as 10% or 25% or 50% or higher.

In another embodiment, a variation of the above, there may be a second compound, suitable for application to human skin, which blocks more total radiation within wavelength range C (320 to 340 nm) than it blocks in wavelength range A, wherein the topical composition blocks a percentage $PE_C$ of radiation in wavelength range C (320 to 340 nm) that is greater than $PE_A$. The percentage $PE_C$ may be defined as:

$$PF_C = 1 - \frac{\int_{320\,nm}^{340\,nm} I(\lambda) \cdot w(\lambda) \cdot T(\lambda) d\lambda}{\int_{320\,nm}^{340\,nm} I(\lambda) \cdot w(\lambda) d\lambda}$$

where $PE_C-PE_A$ is some percentage such as 5%, 15%, or higher.

Another embodiment described herein is a method of delivering, from ambient solar radiation, a dose of EMR within at least a predetermined wavelength band, which may be greater than about 300 nm to the skin of a human subject, comprising the steps of: covering a region of the skin with the topical composition of claim 1; and exposing the person to the ambient solar radiation for a predetermined period of time; and stopping the exposure of the person to the ambient solar radiation after the passage of the predetermined period of time.

Another embodiment described herein is a method of delivering, from ambient solar radiation, a dose of EMR within at least a predetermined wavelength band to the skin of a human subject, comprising the steps of: covering a region of the skin with a topical composition which may allow passage of EMR within at least the predetermined wavelength band; and exposing the person to ambient solar radiation for a predetermined period of time; making a dosage calculator by executing a dosage calculator application program which has been stored in a general purpose digital computer's memory, to impart dosage calculation functionality to the general purpose digital computer by changing the state of the computer's arithmetic logic unit when a set of program instructions of the dosage calculator application program are executed, wherein the program instructions comprise the following steps: obtaining (A) actual or predictive solar radiation data for a place in which the subject is located and a time during which the exposure is occurring or is to occur; obtaining (B) a number or set of numbers representing the UV transmission characteristics of the topical composition within the predetermined wavelength band; and calculating, based on a set of available data which includes (A) and (B), a predetermined period of time reflecting a therapeutically effective amount of exposure time to the ambient solar radiation for treatment of a condition of the human subject in need of therapeutic treatment by exposure to UV light; and stopping the exposure of the person to the ambient solar radiation after the passage of the predetermined period of time. In a particular variation of this embodiment, the set of available data may further include a value or set of values reflecting the skin type of the human subject. In another variation, the general purpose digital computer may be a mobile phone or tablet. In another variation, the general purpose digital computer may be a server comprising a phone-based voice system, wherein the human subject has remote access to the voice system via telephone, and wherein the program instructions may further comprise the step of providing voice-based instructions to the human subject comprising a statement of the predetermined period of time.

Other embodiments are disclosed herein.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification or the common knowledge within this field.

In the drawings, where like reference numerals refer to like reference in the specification.

DETAILED DESCRIPTION

Figure 1:
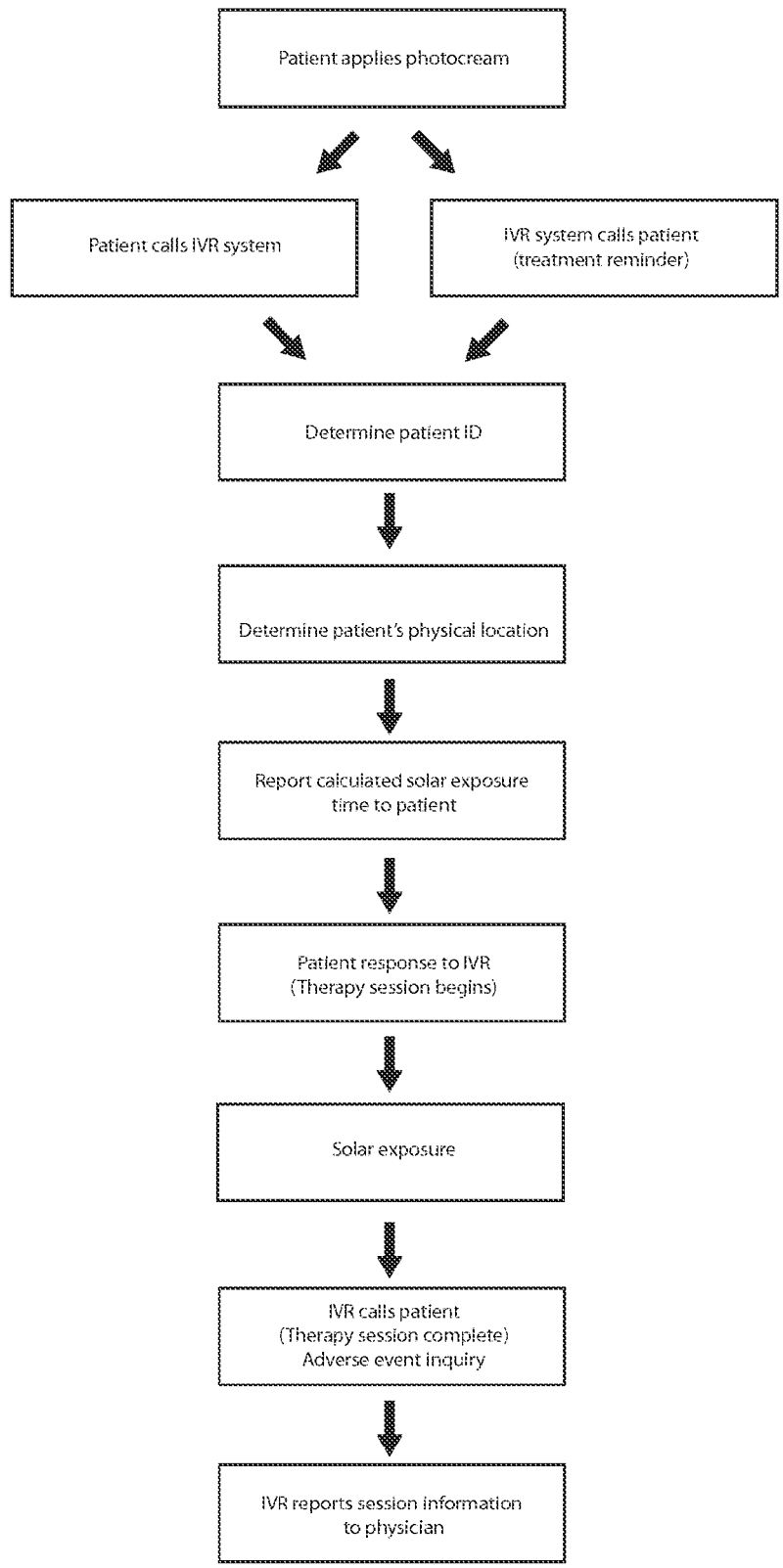
FIG. 1 is a flowchart showing a method for delivering a therapeutic dose of solar UV radiation using a photocream.

The description herein is provided in the context of a system and method for administering a phototherapy. Those of ordinary skill in the art will realize that the following detailed description is illustrative only and is not intended to be in anyway limiting. Other embodiments will readily suggest themselves to such skilled persons having the benefit of this disclosure. Reference will now be made in detail to implementations as illustrated in the accompanying drawings. The same reference indicators will be used throughout the drawings and the following detailed description to refer to the same or like parts.

In the interest of clarity, not all of the routine features of the implementations described herein are shown and described. In the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

As used herein, the term UVB refers to electromagnetic radiation in the range of about 280-320 nm, while UVA refers to radiation in the range of about 320-400 nm. The boundaries of these regions are sometimes slightly varied from these numbers in the literature.

As used herein, the term photocream refers to a composition that, when applied to the skin, filters radiation from a radiation source (e.g., solar radiation) such that it preferentially delivers certain bands of radiation to the skin. A photocream differs from typical sunscreens, in that the latter are usually intended to block predominately all of the UVB and UVA radiation. A photocream may only block portions of the UVB and UVA spectrum.

In one embodiment disclosed herein, a topical composition may be provided, which includes a compound that blocks UV radiation such that the admitted radiation is biased towards a therapeutic range of around 310 nm. To quantify this biasing effect, UV radiation can be divided into two ranges, including a therapeutic range A between about 300 nm and 320 nm, and a non-therapeutic range B between about 280 nm and 300 nm. A percent of radiation blocked for a therapeutic range A may be calculated as follows:

$$PF_A = 1 - \frac{\int_{300 \text{ nm}}^{320 \text{ nm}} I(\lambda) \cdot w(\lambda) \cdot T(\lambda) d\lambda}{\int_{300 \text{ nm}}^{320 \text{ nm}} I(\lambda) \cdot w(\lambda) d\lambda}$$

where $\lambda$ is a wavelength of radiation, $I(\lambda)$ is an intensity of radiation (e.g., a solar irradiance standard ASTM G177-03) passing through a topical composition at a given wavelength in $W/m^2/nm$, $T(\lambda)$ is an experimentally derived mean transmittance of a topical composition, and $w(\lambda)$ is a weighting function defined as:

$$w(\lambda) = \begin{cases} 1 & 280 \text{ nm} < \lambda \le 298 \text{ nm} \\ 10^{0.094(298-\lambda)} & 298 \text{ nm} < \lambda \le 320 \text{ nm} \end{cases}$$

as defined by McKinlay, A. F. and B. L. Diffey (1987), CIE J. 6, 17-22.

A percent of radiation blocked for the non-therapeutic range B may be calculated as follows:

$$PF_B = 1 - \frac{\int_{280 \text{ nm}}^{300 \text{ nm}} I(\lambda) \cdot w(\lambda) \cdot T(\lambda) d\lambda}{\int_{280 \text{ nm}}^{300 \text{ nm}} I(\lambda) \cdot w(\lambda) d\lambda}$$

If $PF_B$ exceeds $PE_A$ by some amount, such as about 10%, 25%, or 50%, there may be a biasing effect towards a therapeutic value of about 310 nm. The measurement of $PE_A$ and $PF_B$ may be performed for an entire photocream composition, which may be in any cosmetic-grade carrier such as a topical lotion, stick, spray, cream, or oil. Alternatively, the measurement may be done with a particular component of the photocream composition, such as hesperidin or other compounds. In such case, the compound may be placed in a UV-transparent solvent while the tests are performed.

Figure 9:
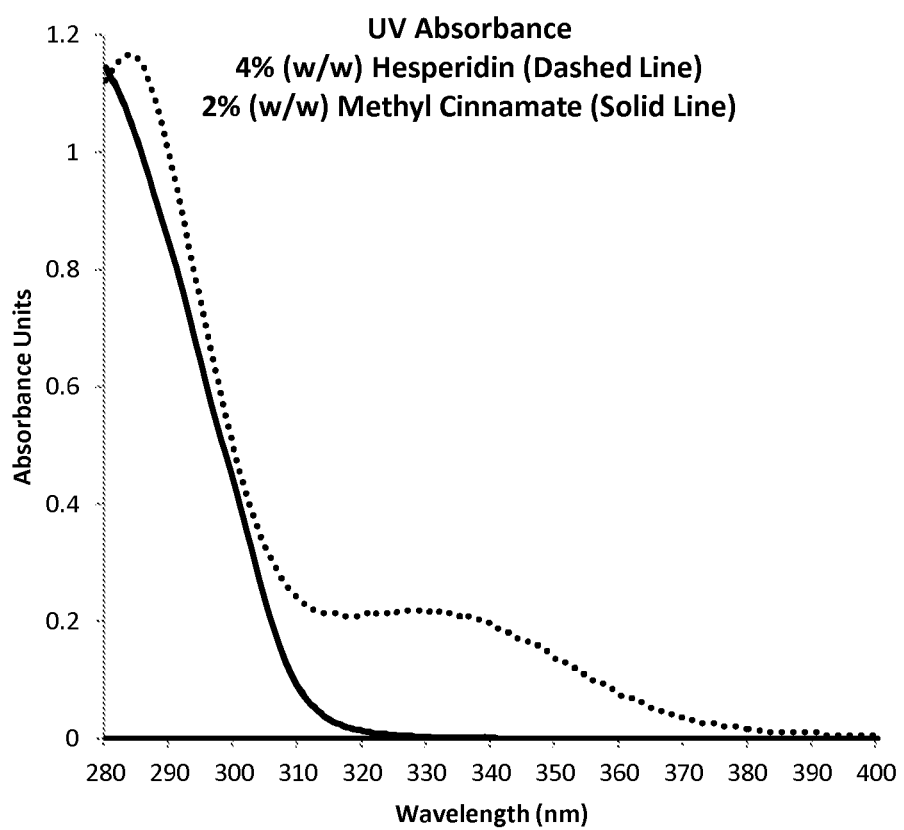
FIG. 9 is a plot showing a UV absorbance profile for an example cream comprising 4 wt. % hesperidin (CAS#520-26-3, dashed line), and a UV absorbance profile for a cream comprising 2% methyl cinnamate (CAS#1754-62-7, solid line) applied at a thickness of 20 µm.
Figure 10:
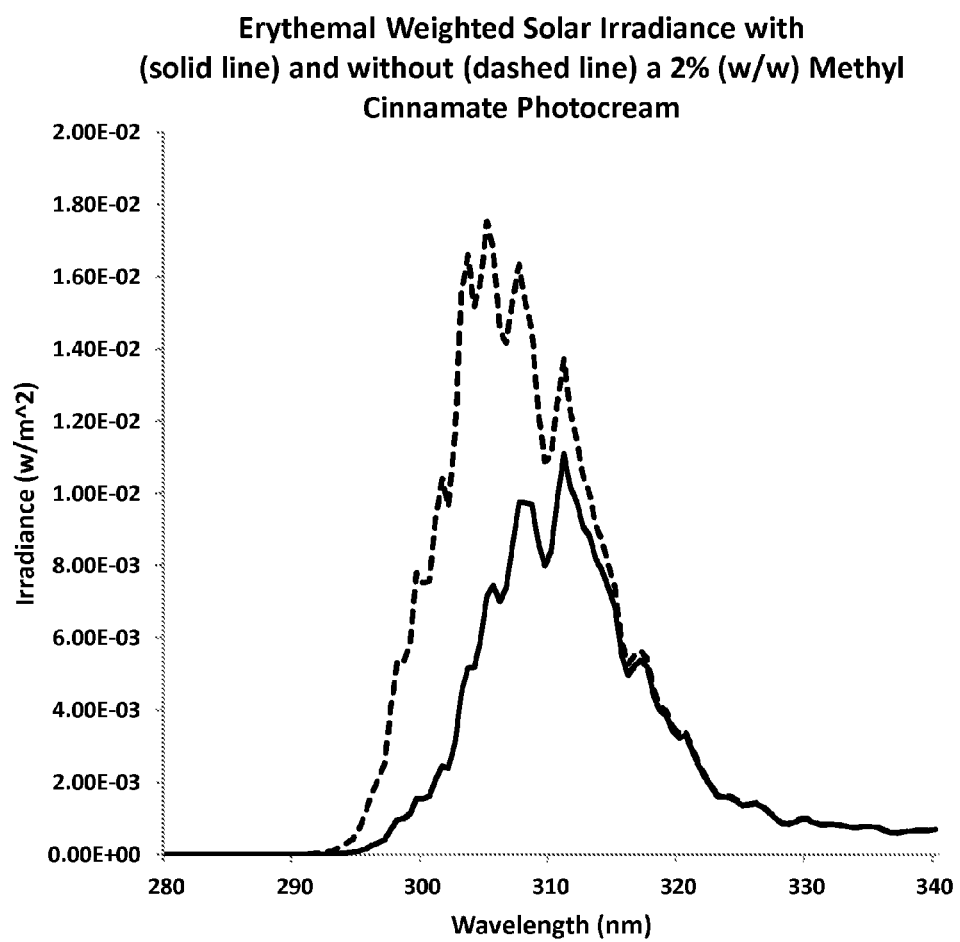
FIG. 10 is a plot showing an erythemally weighted solar irradiance with (solid line) and without (dashed line) an example cream containing 2% methyl cinnamate applied at a thickness of 20 µm.
Figure 12:
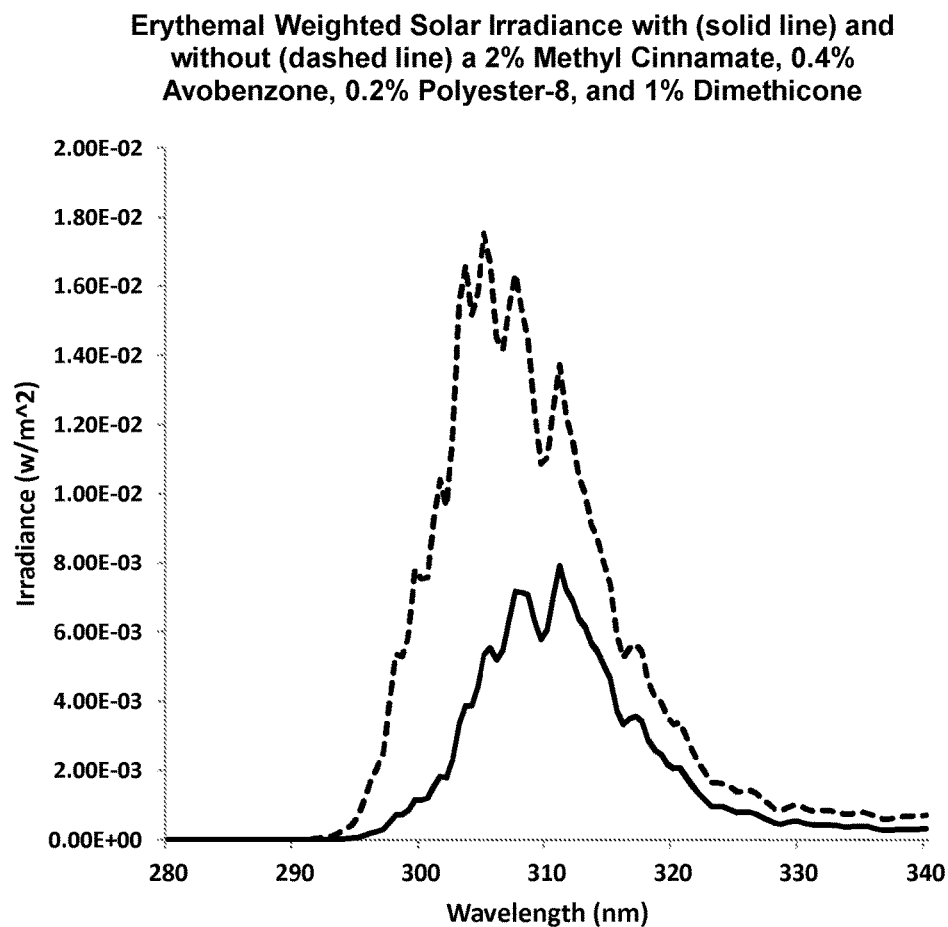
FIG. 12 is a plot showing an erythemally weighted solar irradiance with (solid line) and without (dashed line) an example cream comprising 2 wt. % methyl cinnamate, 0.4% avobenzone, 0.2% polyester-8, and 1% dimethicone applied at a thickness of 20 µm.

Examples of values of $PF_B-PE_A$ may include 24% for the 4% hesperidin formulation described in FIG. 9, 66% for the 2% methyl cinnamate formulation described in FIG. 9, and 44% for the 2% methyl cinnamate cream described in FIG. 12.

Absorption tests for a topical composition on a rough surface such as skin may be performed using the methodology outline in the US FDA Broad Spectrum Test (21 CFR 201.327(j)) (Jul. 5, 2011), which is incorporated by reference herein in its entirety, to produce a mean transmittance function $T(\lambda)$. The mean transmittance $T(\lambda)$ is defined in 21 CFR 201.327(j)(4). Although this standard specifically includes UV measurements in a range 290 nm to 400 nm, one of skill in the art may extend the range to 280 nm in a straightforward manner.

The topical composition above may in one embodiment be further enhanced by the addition of a second component to create a band-pass cream. In such a composition, for example, the second compound may have a protecting effect in a non-therapeutic range C between about 320 nm and 340 nm. A percent of radiation blocked for a non-therapeutic range C may be calculated as follows:

$$PF_C = 1 - \frac{\int_{320 \text{ nm}}^{340 \text{ nm}} I(\lambda) \cdot w(\lambda) \cdot T(\lambda) d\lambda}{\int_{320 \text{ nm}}^{340 \text{ nm}} I(\lambda) \cdot w(\lambda) d\lambda}$$

If $PF_C$ exceeds $PE_A$ by some amount (for example, about 5% or 15%) it may further enhance admitted radiation in the therapeutic range. This may create a band, around 310 nm, in which UV light preferentially passes, while light is blocked above and below that general range.

In one embodiment disclosed herein, a band-pass topical cream may be used to selectively filter radiation in the UVB region of the electromagnetic spectrum. The chemical composition of the topical cream may be such that it absorbs wavelengths of light that are non-beneficial to the treatment of the aforementioned skin diseases. Simultaneously, the band-pass cream may selectively pass wavelengths of radiation that are beneficial for treatment. Application of the cream is followed by exposure to either natural (sun) or artificial light. In various alternative embodiments, the filtering mechanism can be in the form of a topical agent, a film, an article of clothing, a lens, a window glass, or other light filtration mechanism having an equivalent effect.

After application of the photo-filtration device, a person (or other biological organism) could receive a controlled dose of phototherapy throughout a day. This would greatly reduce the inconvenience of the standard method of delivering phototherapy in medical offices. Furthermore, the band-pass cream could be formulated into different dosages depending on the required amount of phototherapy, physiology, genetics of the user or the condition being treated.

A method of delivering a therapeutic dose of UV radiation through a photocream is illustrated in FIG. 1. A patient applies a photocream, and may either call an interactive voice response (IVR) system, or the IVR system may call the patient. The IVR system may also call the patient prior to application of the photocream. The IVR system may determine the patient's ID, as well as the patient's physical location. Based on this information, as well as potentially previous information obtained about the patient and associated with his or her ID, the system may report to the user the calculated solar exposure time.

In one embodiment, the IVR system may indicate when the patient should begin solar exposure (or in another embodiment, exposure to artificial light). Subsequently, when the therapy session is complete, the IVR system may then call the patient to indicate that the therapy session is complete. The IVR may also report the session information to a physician.

Many different scenarios can be imagined to facilitate applying proper therapeutic dosage to a patient wearing a photocream, for example, a similar system to the previously defined IVR method could be derived using SMS technology or a mobile application. In a scenario where a phone-based voice system (which may include, for example, POTS, VOIP, or other network voice communication) is used, the following steps could be implemented: 1) The system may initiate a phone call as a reminder for therapy or the user may directly call the system and an interactive voice response system answers. 2) The service identifies the user based on the phone number on file or the user enters a user specific ID or the user is forwarded to a representative to help identify the user. 3) The user is given the option to use the zip code on file or enter a new zip code for the current session. 4) The system calculates the session time and reports the time in minutes to the user. 5) The user hangs up. 6) The system calls the user back after the therapy time is completed. If the user does not answer or a voice mail service is reached, the system re-calls. 7) The user confirms that the session was completed. 8) The user is asked if he/she had any adverse events. 9) The system logs the session.

In another embodiment, the above procedure may be used, except that instead of an IVR, the patient may use a mobile application, and the mobile application may provide the necessary notifications and collect the necessary information.

In each of the aforementioned embodiments, which may include an IVR system, SMS technologies, mobile application, or other computer terminal assisted method of delivering a therapeutic dose of radiation using a photocream, a computed therapy time based on available weather and solar radiation data for that user's location (global position) and time of day is required. This data when combined with the analytical profile (i.e., UV absorption/transmittance properties) of the photocream and the profile of the patients skin (e.g., Fitzpatrick skin type) can be used to calculate an appropriate exposure limit for that patient to receive phototherapy. Diurnal UV data is possible to calculate based on a number of predictive models, for example, the CART regression model. Such models may depend on a number of input parameters including: surface albedo, cloud cover, ozone profile, aerosol properties, altitude, total ozone, sun to earth distance, and temperature. Such input parameters are currently available (e.g., from the national weather service); thus, UV predictive models can be made for most locations on earth. There are already web services that provide such data (e.g., www.uvawareness.com). The use of global positioning technology (e.g., from a mobile device) or any other location information can be used to facilitate this method.

Figure 11:
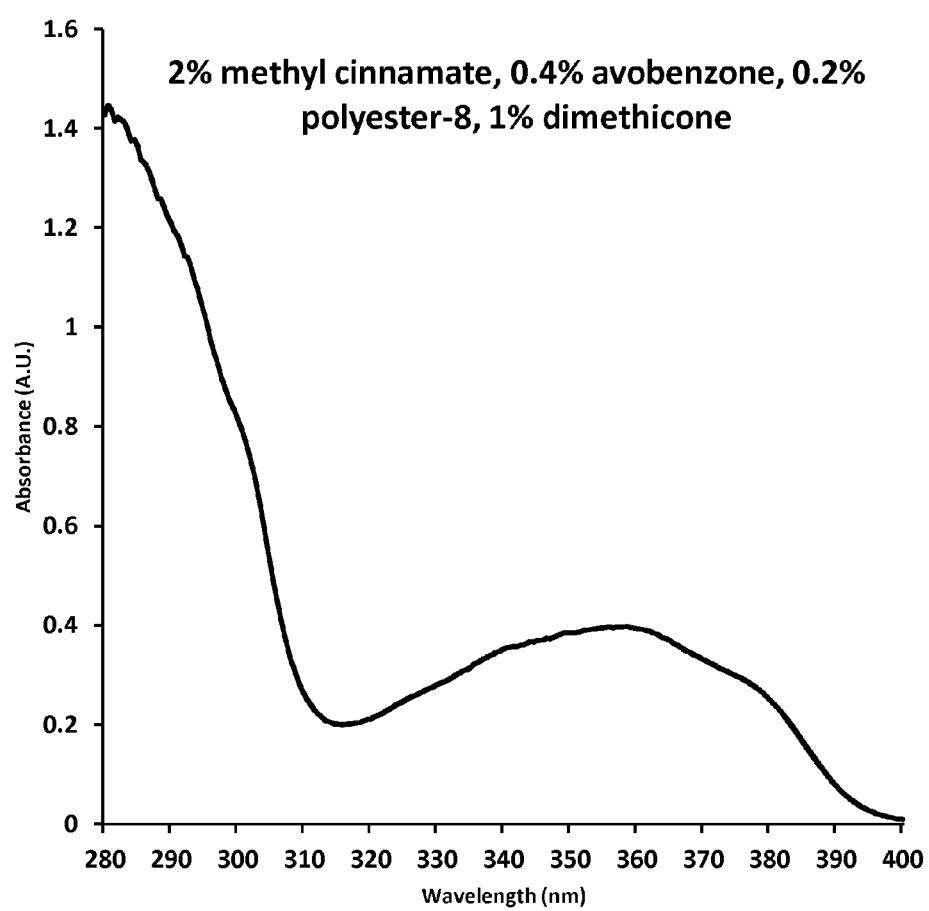
FIG. 11 is a plot showing a UV absorbance profile for an example cream comprising 2% methyl cinnamate, 0.4% avobenzone, 0.2% polyester-8, and 1% dimethicone, applied at a thickness of 20 µm.

In one scenario of applying proper therapeutic dosage to a patient wearing a photocream, a patient will first obtain a photocream from a physician. For example, a photocream delivering NB-UVB therapy may be formulated with 2% (w/w) methyl cinnamate (CAS#103-26-4), 0.4% (w/w) avobenzone (CAS#70356-09-1), 0.2% (w/w) polycrelene (CAS#862993-96-2), 1% (w/w) dimethicone (CAS#63148-62-9), and 1% (w/w) colloidal oatmeal (CAS#84012-26-0). Such a photocream will have an experimentally derived absorbance spectrum (FIG. 11), from which a solar-UV biasing profile (FIG. 12) and an adjusted SPF (e.g., SPF 2.1) can be determined. The physician can report this value, the patient's Fitzpatrick skin type and the physician's recommended therapeutic dosage (i.e., percent of the minimal erythemal dose (MED)) to an internet web service. The patient will be supplied a unique user ID for this web service in order to access the prescribed therapy exposure times in the future. At the time of therapy, the patient can use a mobile computer terminal or mobile application equipped with a global positioning system or other inputted location information to access this web service. Once the unique identity of the user is determined from the log-in ID, the website will determine the appropriate exposure time for that patient based on: the patient's current physical location (determined from GPS or any other location information), time of day (acquired from mobile device or entered by the user), the input parameters needed for the UV profile model (obtained from an outside source, e.g., the national weather service) and the physician's data. Therapy sessions can then be logged and reported back to the physician via the same web service.

As an example, a psoriasis patient (Patient 1) visits a doctor's office and is prescribed a photocream for the treatment of psoriaisis. The doctor determines that Patient 1 is Fitzpatrick skin-type 2 and should have 75% of the MED at each therapy session. The doctor uses a computer to log on to a web service and create a user ID for Patient 1, to which he ascribes his diagnosed Fitzpatrick skin-type II and recommendation of 75% of the MED at each therapy session to Patient 1's ID. The doctor then provides Patient 1 with the unique ID for the web service. Patient 1 decides to conduct a therapy session on Aug. 1, 2013 at 12:01 PM in Irvine, Calif. 92614. Prior to the therapy session, Patient 1 applies a photocream. Using a mobile computing device, Patient 1 logs on to the web service using his unique ID. Once logged on to the web service the mobile device reports to the web service the patient's global and temporal location (Aug. 1, 2013, 12:01 PM in Irvine, Calif. 92614). The web service then makes an API call to another web service that provides UV data derived from global location (one such site is www.uvawareness.com). Using the ultraviolet index (UVI) data provided by the API call, the web service will use a computer algorithm to extrapolate the UVI data to a continuous function of time of the form:

$$UVI_t = UVI_o \cos Z$$

where $UVI_o$ is the maximum UVI at a location occurring at solar noon and Z is the zenith angle defined by:

$$Z = \cos^{-1}(\sin \phi \sin \delta + \cos \phi \cos \delta \cos \omega_s)$$

where the angles $\phi$ and $\delta$ are latitude and solar declination (i.e., global position) and $\omega_s$ is the hour angle defined by, $$\omega_s = \frac{\pi}{12}(t_s - 12) \text{ (radians)}$$

where $t_s$ is the solar time in hours. From this algorithm continuous diurnal UVI data can be approximated. The computer algorithm will then calculate the appropriate exposure time by integrating the function $UVI_t$ over enough time to give the predetermined energy exposure.

Since, Patient 1 is Fitzpatrick skin type II, the recommended maximum exposure is defined by the world health organization at 250 J/m². The doctor has recommended only 75% exposure and the photocream will have an experimentally derived absorbance profile (e.g., an SPF of 2.2). From this data the proper exposure time can be derived by numerically solving for $t_f$ in the following expression:

$$\int_{t_o}^{t_f} UVI_t dt = 250 \text{ J/m}^2 \times 0.75 \times 2.2 = 412.5 \text{ J/m}^2$$

For Patient 1's session on Aug. 1, 2013, 12:01 PM in Irvine, Calif. 92614 the predicted $t_f$ is 0.38 hours or approximately 23 minutes.

In a further embodiment, a computed analysis may also be used to select the optimum band-pass photocream concentration and/or light dosage based on the patient's response to a given concentration of the photocream with or without other characteristics of physiology or genetics of the user. According to such an approach, a method for predicting optimum photocream concentration may include: (a) constructing a N-layer neural network; (b) training the neural network with a data set of patients who have characteristics that relate to response to the photocream for the treatment of dermatological conditions, such as vitiligo, psoriasis, atopic dermatitis, etc.; (c) obtaining an image of skin response from the subject, including concentration of the photocream and light dosage; (d) generating a response-based profile from the sample, the profile being a function of values associated with a prescribed set of phototherapy parameters; (e) obtaining a difference vector from the profile; (f) inputting the difference vector into the neural network. The necessary patient data may be able to be collected from a personal device and automatically supply real time monitoring and adjustments.

In an alternative embodiment to a computer terminal assisted method of delivering a therapeutic dose of radiation using a photocream, a direct feedback (UV measuring device or dosimeter) method may be used.

In one embodiment, a dosimeter device may measure both therapeutic radiation and non-therapeutic radiation, or either of them separately. Furthermore, a wearable device in the form of an adhesive UV dosimeter appliqué could be used to monitor the amount of radiation exposure a person has received. The UV dosimeter appliqué could be applied to the skin prior to addition of the band-pass photocream and would itself be treated with the cream; in another embodiment, the UV dosimeter appliqué could be treated with a polymer coating containing the same or similar (having closely related UV absorbance) chemical actives as the band-pass photocream. The photocream concentration may then be adjusted as necessary.

Delivery of UV light may be provided by sunlight, a UV lamp, a fluorescent tube, or through the amplification of available light such as through fluorescence energy transfer reaction (FRET), chemical, molecular, or other approaches known in the art.

Figure 2:
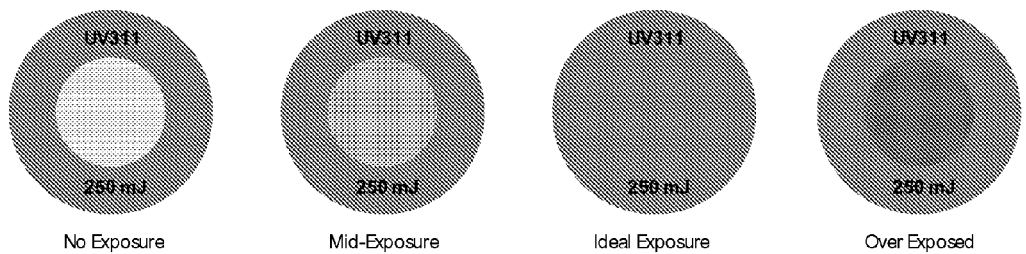
FIG. 2 is a diagram illustrating an embodiment of a UV dosimeter appliqué.
Figure 2:
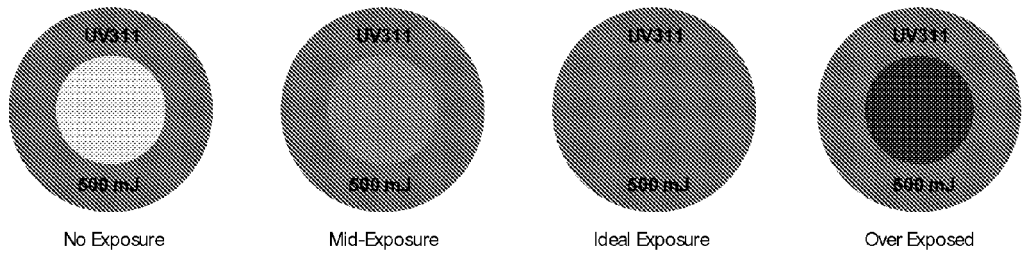

FIG. 2 illustrates an embodiment of a UV dosimeter appliqué. Two halves of a geometric shape may be used to report proper dosage of therapeutic UVB exposure. In one half of the geometric shape, a UV reactive dye may be printed. The chemistry of the dye may be such that the dye will change color in a UV dosage dependent manner. The color change of the dye may be calibrated, empirically, in a controlled laboratory environment by exposing the printed dye to a known amount of UV radiation. The empirically observed color may then be printed with standard dyes (non-UV reactive) onto the outer half of the geometric shape. This arrangement would allow for ease of use by the user in correlating color change with proper UV dosage. The UV dosimeter appliqué may be replaced with a similar device, such as a wristband, ring or a watch.

In another embodiment of the UV dosimeter appliqué, two or more UV-reactive inks may be used to create a dosimeter that reports exposure to different bands of UV radiation. Each UV-reactive ink may have chemistry such that each ink would absorb UV radiation at separate bands (i.e., would change color based on the absorption of UV radiation at different wavelengths). As such, the system could be used to monitor exposure to UV radiation that would be considered therapeutic for a particular skin condition versus radiation that would be considered non-therapeutic. Alternatively, a therapeutic versus non-therapeutic determining dosimeter could be constructed using a broadband UV absorbing dye that is treated with different polymer coatings containing UV absorbing actives that would filter out either therapeutic or non-therapeutic UV radiation. The dosimeter is not limited to a chemical dosimeter, but could in one of several embodiments employ an electronic photosensor.

In yet another embodiment, a photoactive molecule may be added to the photocream; said molecule may change its chemical structure after a threshold level of UV exposure such that it would become opaque to UV radiation after receiving an appropriate dosage. As such, the added molecule would protect (block) the user from further exposure. This may be a manner in which, the band-pass photocream concentration is adjusted as required for optimum treatment benefits. The adjustments can be made based upon a database of patient conditions, treatment response, physiology, or genetics of the user and state of a device or other input and/or computer analysis.

Figure 3:
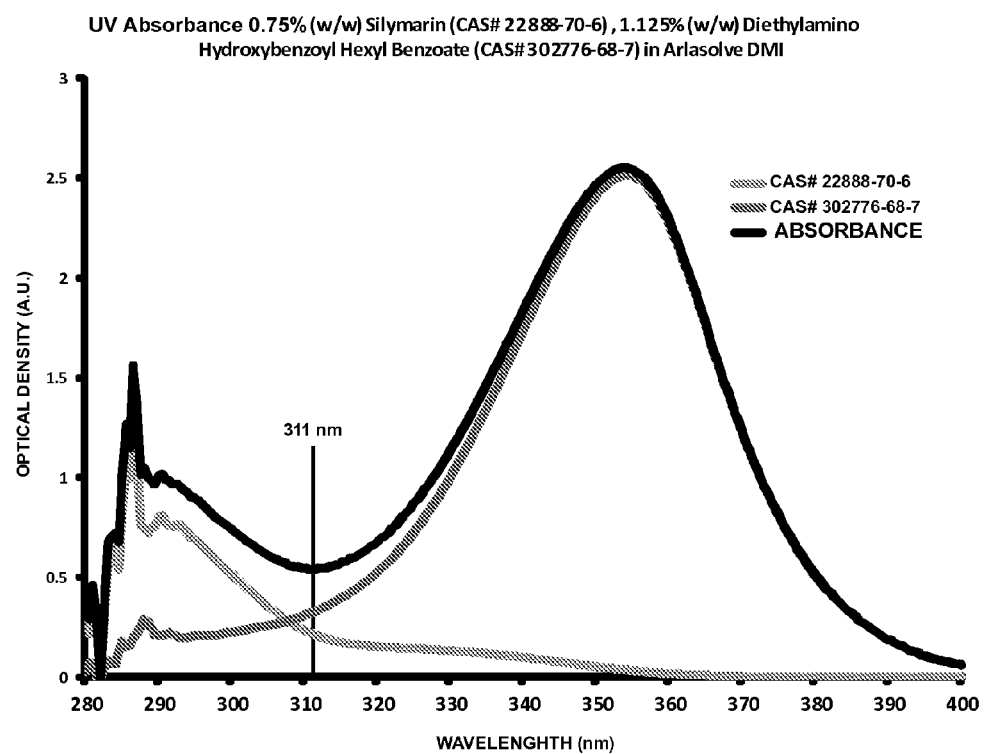
FIG. 3 is a plot showing examples of absorbance spectra of a photocream containing 0.75% (w/w) silymarin (CAS#22888-70-6) and 1.125% (w/w) diethylamino hydroxybenzoyl hexyl benzoate (CAS#302776-68-7).
Figure 4:
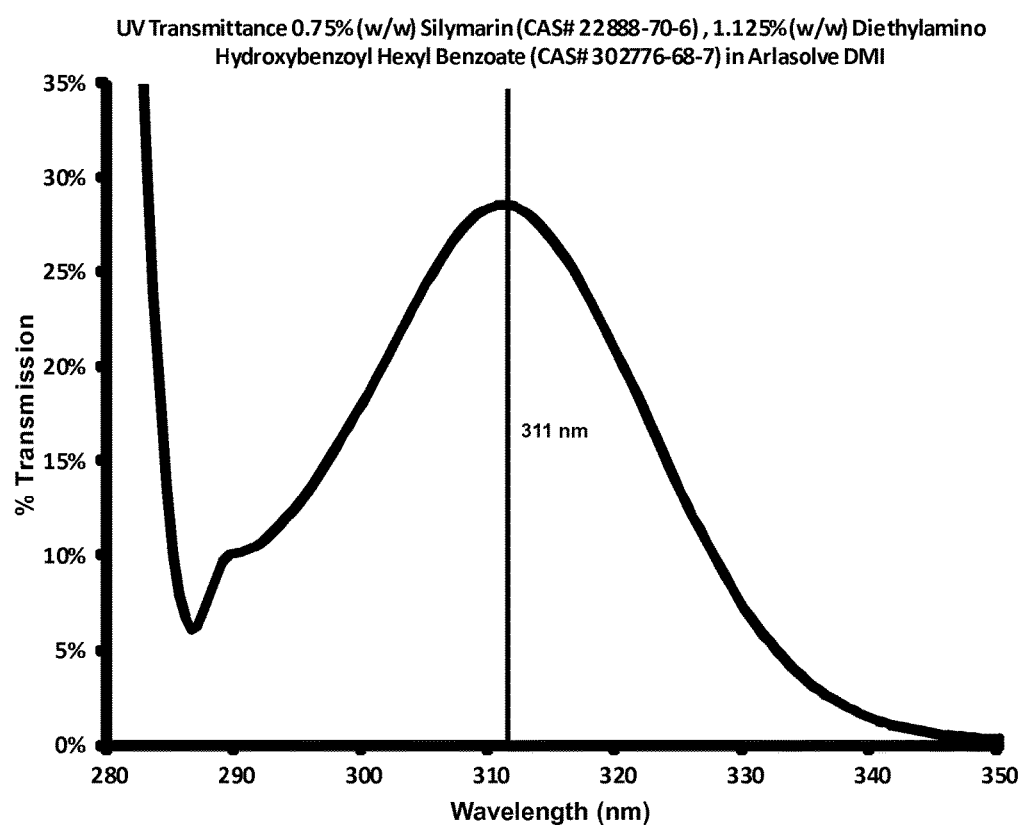
FIG. 4 is a plot showing the transmittance of a band-pass photocream.

In one embodiment of the present invention, a band-pass photocream is composed such that it is optimized to have maximum transmittance at a therapeutic wavelength of 311 nm for the treatment of vitiligo, psoriasis, atopic dermatitis, and other skin conditions. Said photocream would contain two UV absorbing active ingredients having UV absorbance spectra that when combined in a determined ratio would have a spectral minimum (valley) at 311 nm. For example, a band-pass photocream could be formulated with silymarin (CAS#22888-70-6) and diethylamino hydroxybenzoyl hexyl benzoate (CAS#302776-68-7) in a weight to weight ratio of 2:3 (or less preferably within the range 1:2 to 5:6, or within the range 5:9 to 7:9) to produce an absorbance spectrum with a spectral valley at 311 nm. Said photocream may contain 0.75% (w/w) silymarin (CAS#22888-70-6) and 1.125% (w/w) diethylamino hydroxybenzoyl hexyl benzoate (CAS#302776-68-7). An illustrative absorbance spectrum for such a composition is shown in FIG. 3 when applied at a thickness of 20 µm. From the UV absorbance spectrum in FIG. 3, a transmittance profile for a band-pass photocream may be determined as illustrated in FIG. 4, which in this example indicates a maximum transmittance (about 29%) at 311 nm. Alternatively, a band-pass photocream could be formulated with alpha-glucosyl hesperidin (CAS#161713-86-6) and diethylamino hydroxybenzoyl hexyl benzoate (CAS#302776-68-7) in the weight to weight ratio of 4:1 (or less preferably within the range 3:1 to 5:1, or within the range 7:2 to 9:2) to produce an absorbance spectrum with a spectral valley at 311 nm.

Figure 5:
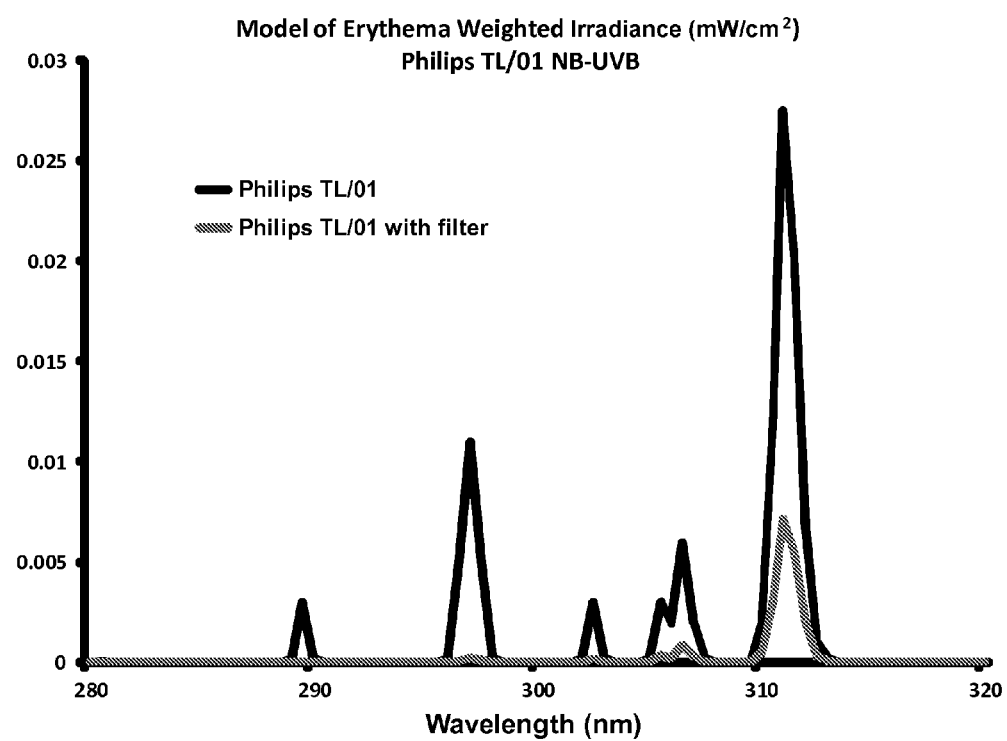
FIG. 5 is a plot representing an example of the wavelength dependent erythemally weighted irradiance of a NB-UVB lamp (Philips TL/01) with and without a 2% silymarin photocream applied at a thickness of 20 µm.

Typical light sources for the treatment of psoriasis and vitiligo (e.g., Phillips TL/01) have been reported to deliver approximately 66% of their erythemally weighted irradiance in the therapeutic range 310-320 nm. The remaining erythemally weighted irradiance (34%) may be delivered at wavelengths below 310 nm, which can have negative health consequence for users (e.g., erythema and cancer). An example representing the wavelength dependent erythemally weighted irradiance is shown in FIG. 5.

Figure 6:
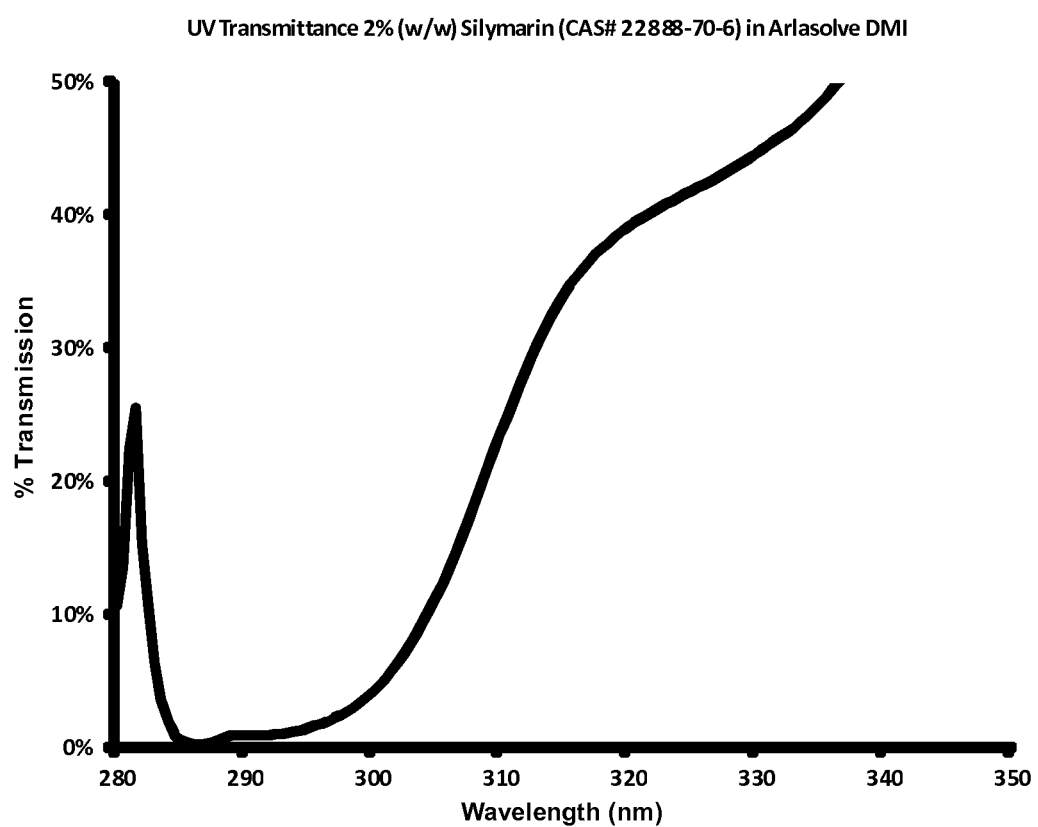
FIG. 6 is a plot showing an example UV transmittance spectrum of a photocream formulated with 2% (w/w) silymarin (CAS#22888-70-6), when applied at a thickness of 20 µm.

In another embodiment, a combination of UV absorbing molecules may be formulated to selectively filter non-therapeutic wavelengths of light from an artificial light source. The filtering mechanism can be in the form of a topical agent, a film, an article of clothing, a lens, or other light filtration mechanism having an equivalent effect. For example, a photocream may be formulated with 2% (w/w) silymarin (CAS#22888-70-6) and would produce the UV transmittance spectrum in FIG. 6 when applied at a thickness of 20 µm. From the UV transmittance spectrum in FIG. 6, an adjusted erythemally weighted irradiance of the phototherapy lamp in (FIG. 5) may be calculated, and in this example predicts delivery of 87% of the erythemally weighted irradiance in the therapeutic range 310-320 nm.

The above exemplary mode of carrying out the invention is not intended to be limiting as other methods of initiating a filter between the radiation source and radiation destination are possible. For example, a similar chemistry to the photocream described above can be incorporated into a polymer coating and applied directly to a fluorescent tube or embedded in a screen placed between the radiation source and the intended radiation destination.

In one embodiment, a band-pass therapeutic cream that selectively passes UVB light in the range 306-310 nm can be formulated for the production of vitamin D in human skin. This region (306-310 nm) has the greatest offset of benefit for the production of vitamin D versus the negative effects of erythema. Therefore, this embodiment would provide limited protection from the deleterious effects of sun exposure (erythema) while still allowing natural synthesis of vitamin D in skin.

Figure 7:
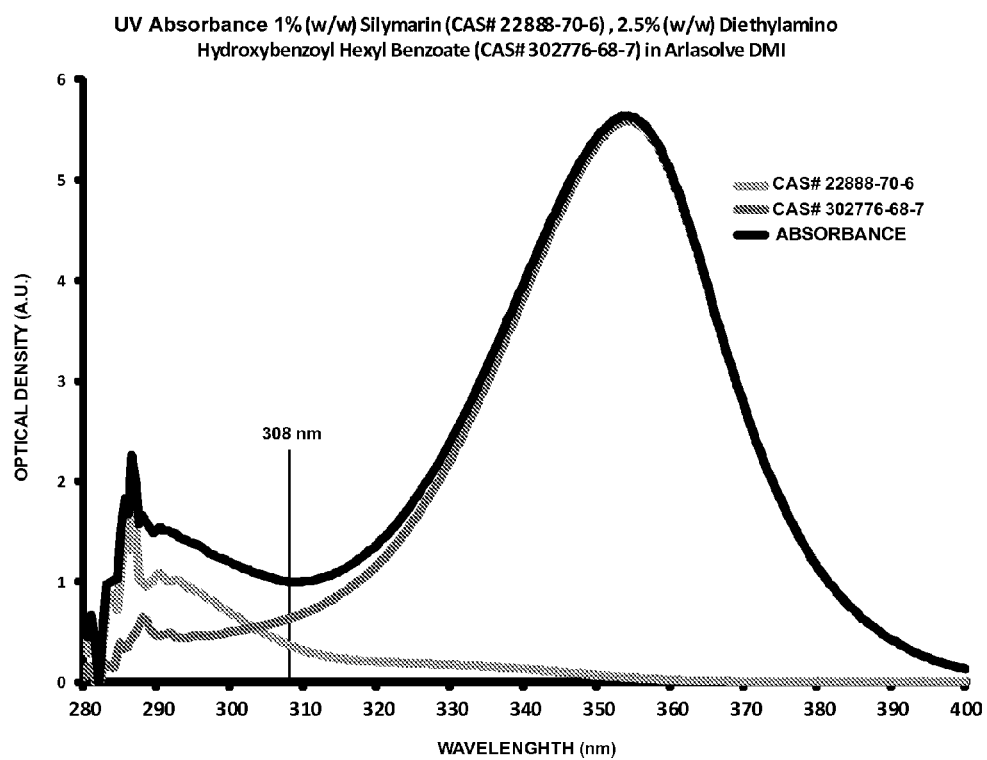
FIG. 7 is a plot showing an example absorbance spectrum of a photocream containing 1% (w/w) silymarin (CAS#22888-70-6) and 2.5% (w/w) diethylamino hydroxybenzoyl hexyl benzoate (CAS#302776-68-7), when applied at a thickness of 20 µm.
Figure 8:
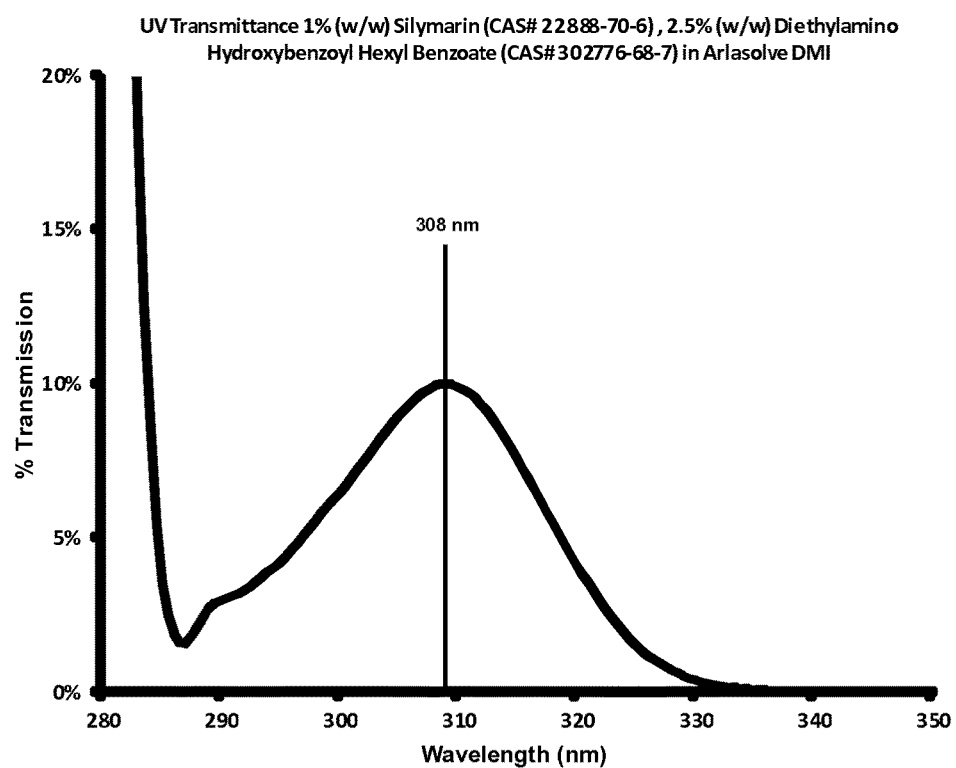
FIG. 8 is a plot showing the transmittance of a band-pass photocream determined from the UV absorbance spectrum of FIG. 7.

In yet another embodiment, a combination of UV absorbing molecules may be formulated to selectively pass UVB light in the range 306-310 nm for the benefit of maximum vitamin D production while still providing limited protecting from erythema. Said photocream may contain two UV absorbing active ingredients having UV absorption spectra that when combined in a determined ratio would have a spectral minimum (valley) at 308 nm. For example, a band-pass photocream could be formulated with silymarin (CAS#22888-70-6) and diethylamino hydroxybenzoyl hexyl benzoate (CAS#302776-68-7) in a weight to weight ratio of 2:5 (or less preferably within the range 3:10 to 1:2, or within the range 1:3 to 7:15) to produce an absorbance spectrum with a spectral valley at 308 nm. Said photocream could contain 1% (w/w) silymarin (CAS#22888-70-6) and 2.5% (w/w) diethylamino hydroxybenzoyl hexyl benzoate (CAS#302776-68-7) and would produce an absorbance spectra shown in FIG. 7 when applied at a thickness of 20 µm. From the UV absorbance spectrum in FIG. 7, a transmittance profile for a band-pass photocream can be determined as exemplified in FIG. 8, which in this example indicates a maximum transmittance (about 10%) at 308 nm. Alternatively, a band-pass photocream could be formulated with alpha-glucosyl hesperidin (CAS#161713-86-6) and diethylamino hydroxybenzoyl hexyl benzoate (CAS#302776-68-7) in a weight to weight ratio of 3:2 (less preferably a range of 5:4 to 7:4, or a range of 4:3 to 5:3) to produce an absorbance spectrum with a spectral valley at 308 nm.

Other combinations of UV absorbing actives are possible to achieve similar results to those described in the above disclosures. Examples of comparable UV absorbing active include but are not limited to: hesperidin (CAS#520-26-3), methyl cinnamate (CAS#103-26-4), vinblastine (CAS#865-21-4), acteoside (CAS#61276-17-3), acacetin 7-O-rutinoside (CAS#480-36-4), phytoene (CAS#13920-14-4), poncirin (CAS#14941-08-3), gambogic acid (CAS#2752-65-0), chaetoglobosin (CAS#50335-03-0), poliumoside (CAS#94079-81-9), sitosteroline (CAS#474-58-8), naringin (CAS#10236-47-2), pentagalloyl glucose (CAS#14937-32-7), amentoflavone (CAS#1617-53-4), tetrandrine (CAS#518-34-3), isoacteoside (CAS#61303-13-7), (–)-phaeanthine (CAS#1263-79-2), garcinol (CAS#78824-30-3), salvianolic acid B (CAS#121521-90-2), docetaxel (CAS#114977-28-5), ecdysterone (CAS#5289-74-7), glycyrrhizic acid monosodium salt (CAS#11052-19-0), kaempferol (CAS#81992-85-0), paclitaxel (CAS#33069-62-4), silymarin (CAS#22888-70-6), isoacteoside (CAS#61303-13-7), linarin (CAS#480-36-4), pectolinarin (CAS#28978-02-1), rutin (CAS#153-18-4), kaempferol-3-O-rutinoside (CAS#17650-84-9), diosmin (CAS#520-27-4), rhoifolin (CAS#17306-46-6), avobenzone (CAS#70356-09-1), alpha glucosyl hesperidin (CAS#161713-86-6), caffeine (CAS#58-08-2), mycosporine-like amino acids, and rare-earth metals. Variants of these components may also be used, as well as other substances known to absorb EMR, and preferably ultraviolet light. These substances may be used alone, or in combination with each other. A cream that comprises only one of these substances may not be a band-pass cream as described herein; however, it may still bias radiation towards a therapeutic range of wavelengths.

Many schemes may be implemented for synthesizing new molecules that comprise a band-pass photocream. For example, a molecule may be selected such that its absorbance maximum corresponds to the wavelength of the most therapeutic value (e.g., 310 nm); said molecule could be synthesized such that a conjugated bond may be added to the molecule; in conjunction, a second molecule would be synthesized such that a conjugated bond would be subtracted from the original molecule. In each of the synthesis schemes described above the absorption maxima of the molecule would be red-shifted or blue-shifted accordingly (i.e., increased in wavelength or decreased in wavelength). As such, an equal molar combination of the molecules would produce a filter with an absorbance minimum (valley) close to or at the wavelength of the absorption maximum of the original molecule.

In another embodiment, a photocream is constructed such that it has a fluorophor that fluorescently emits light, followed with exposure to either natural (sun) or artificial light. A fluorescent molecule can be used to develop radiation at a therapeutic wavelength for phototherapy. For example, in the case of acne phototherapy, approximately blue light (450-495 nm) may be employed. In particular, light within the wavelength of about 405-470 nm is known to have a therapeutic effect. A molecule can be selected that would absorb light from non-therapeutic wavelengths of the solar irradiance spectrum and emit light at a therapeutic wavelength. An example of one such a molecule is 7-diethyl-amino-4-methylcoumarin (CAS#91-44-1), a molecule that absorbs at a maximum of 375 nm and fluoresces at a maximum wavelength of 445 nm. The fluorophor can be arranged in a cream or doped into a film or filter that can be place in-between a person (or other life) and radiation emitted from the sun or artificial light source.

In one practical arrangement of the above embodiment, a cream that blocks at least the UVA and UVB radiation (290-400 nm) but transmits visible radiation (400-700 nm) can first be applied to the skin to protect the skin from UV damage. Many such creams are commercially available as broad-spectrum sunscreens, which may for example have sun protection factors (SPFs) of 15, 30, 50, or higher. A second spray or cream could then be applied as a second layer containing a fluorescent compound such as 7-diethyl-amino-4-methylcoumarin. This combined application would have the properties of converting harmful UV radiation into therapeutic blue light, which would pass with endogenous blue light to the skin when exposed to solar irradiance. This exemplary mode would have the additional benefit of improving the absorbance properties (absorbance maximum) of compounds in the second applied layer because they would be applied on a smooth surface (i.e., small depressions on the rough surface of the skin would be filled with sunscreen).

In another embodiment, selective treatment with UVB radiation may be used to treat chronic or acute pruritus. It is known that UVB is immunosuppressive, and that pruritus may be treated by immunosuppression. UVA has also been found to be immunosuppressive. See Phan, Tai A. et al. (2006), Spectral and dose dependence of ultraviolet radiation-induced immunosuppression, *Frontiers in Bioscience* 11, 294-411. Therefore, pruritus may be treated by the use of a topical cream that includes a band gap allowing passage of UVA and/or UVB radiation.

A person of ordinary skill in the art will be able to determine an effective dose for immunosuppression, based on the patient's skin type and the wavelength of light used. It is typically calculated as a fraction of the minimal erythemal dose (MED), which can be derived empirically for each patient. For NB-UVB light, a typical MED would be in the range of about 100-400 mJ/cm$^2$. For broadband-UVB (BB-UVB), a typical range would be about 10-30 mJ/cm$^2$.

In another specific embodiment, hesperidin (CAS#520-26-3) may be used in a cream or powder with or without another UV absorbing component (such as any one of the components described above, and in one example those components that preferentially block EMR above a predetermined wavelength) to treat the aforementioned skin conditions. FIG. 9 (dashed line) is a plot showing a UV absorbance profile for a cream containing, by weight, 4% alpha glucosyl hesperidin, 1% dimethicone, 0.4% carbomer interpolymer type A (allyl sucrose crosslinked), 2% propanediol, 0.1% disodium EDTA, 11% 2-ethylhexyl benzoate, 3% dimethyl isosorbide, 2.25% cetostearyl alcohol, 1% shea butter, 1% safflower oil, 1.75% glyceryl monostearate, and 1% 1,2-hexanediol, applied at a thickness of 20 μm (in water, adjusted with triethanolamine to a pH between 6.0 and 6.5). Hesperidin exhibits significant absorbance in the lower UVB range below roughly 310 nm. A photocream comprising hesperidin without another significant UV absorber will exhibit significant UVB absorption, but also allow UVB transmission at therapeutic wavelengths such as, for example, approximately the 310-320 nm range.

In another specific embodiment, methyl cinnamate (CAS#1754-62-7) may be used in a cream with or without another UV absorbing component (such as any one of the components described above, and in one example those components that preferentially block EMR above a predetermined wavelength) to treat the aforementioned skin conditions. FIG. 9 (solid line) is a plot showing a UV absorbance profile for a cream containing 2% (w/w) methyl cinnamate applied at a thickness of 20 μm. Methyl cinnamate exhibits significant absorbance in the lower UVB range below roughly 310 nm. A photocream comprising methyl cinnamate without another significant UV absorber will exhibit significant UVB absorption, but also allow UVB transmission at therapeutic wavelengths such as, for example, approximately the 310-320 nm range.

FIG. 10 is a plot showing changes in the erythemally weighted solar irradiance with the use of an example cream containing 2% (w/w) methyl cinnamate applied at a thickness of 20 μm. The data shows a standard data set for solar UV irradiance (ASTM 177) weighted by the erythemal action spectrum (FIG. 10 dashed trace) and the same standard data set weighted by the erythemal action spectrum multiplied by the experimentally determined mean transmittance of a 2% (w/w) methyl cinnamate cream applied at a thickness of 20 μm (FIG. 10 solid line). In this example, the use of methyl cinnamate shifts the erythemally weighted radiation maximum to approximately 311 nm within a therapeutic range of 306-315 nm.

FIG. 11 is a plot showing a UV absorbance profile an example cream containing, by weight: 2% methyl cinnamate, 0.4% avobenzone, 0.2% polyester-8 (1400 MW, cyanodiphenylpropenoyl capped), 1% dimethicone, 0.4% carbomer interpolymer type A (allyl sucrose crosslinked), 2% propanediol, 0.1% disodium EDTA, 10% 2-ethylhexyl benzoate, 2% dimethyl isosorbide, 2% cetostearyl alcohol, 1% shea butter, 1% safflower oil, 1.5% glyceryl monostearate, and 1% 1,2-hexanediol, applied at a thickness of 20 μm (in water, adjusted with sodium hydroxide to a pH between 6.0 and 6.5)

Methyl cinnamate exhibits significant absorbance in the lower UVB range below roughly 310 nm. Avobenzone exhibits significant absorbance in the UVA. A photocream comprising methyl cinnamate and avobenzone without another significant UV absorber will exhibit significant UVB and UVA absorption, but also allow UVB transmission at therapeutic wavelengths such as, for example, approximately the 310-320 nm range.

FIG. 12 is a plot showing changes in erythemally weighted solar radiation with the use of the cream described in FIG. 11. The data shows a standard data set for solar UV irradiance (ASTM 177) weighted by the erythemal action spectrum (FIG. 12 dashed trace) and the same standard data set weighted by the erythemal action spectrum multiplied by the experimentally determined mean transmittance of a 2% methyl cinnamate, 0.4% avobenzone, 0.2% polycrelene, 1% dimethicone, and 1% colloidal oatmeal cream applied at a thickness of 20 μm (FIG. 12 solid line). In this example, the use of the cream shifts the erythemally weighted radiation maximum to approximately 311 nm within a therapeutic range of about 306-315 nm.

Other cinnamates may similarly be used, and will have similar UV absorption profiles. This may include, without limitation, ethyl, isobutyl, and tert-butyl cinnamate or any other ester derivative of a cinnamate, which does not alter the optical properties of the molecule (i.e., absorbance maximum of about 278 nm).

The above are example modes of carrying out the invention and are not intended to be limiting. It will be apparent to those of ordinary skill in the art that modifications thereto can be made without departure from the spirit and scope of the invention as set forth in the following claims.

What is claimed is:

1. A method of treating a human patient suffering from psoriasis, vitiligo, atopic dermatitis, and/or pruritis, comprising:

delivering, from ambient solar radiation, a dose of EMR to skin of a human subject by:

covering a region of the skin with a topical composition;

exposing the human subject to the ambient solar radiation for a predetermined period of time to generate an erythemally weighted irradiance therapeutic response; and stopping the exposure of the human subject to the ambient solar radiation after the passage of the predetermined period of time;

wherein the topical composition comprises:

a cosmetic-grade carrier suitable for application to the human skin;

a first compound, suitable for application to human skin, which blocks more total radiation within wavelength range B (280 to 300 nm) than it blocks in wavelength range A (300 to 320 nm); and a second compound, suitable for application to human skin, which blocks more total radiation within wavelength range C (320 to 340 nm) than it blocks in wavelength range A wherein:

the topical composition blocks a percentage $PF_B$ of radiation in wavelength range B that is greater than a percentage $PF_A$ of radiation blocked in wavelength range A, $PF_A$ is defined as:

$$PF_A = 1 - \frac{\int_{300\,nm}^{320\,nm} I(\lambda) \cdot w(\lambda) \cdot T(\lambda) d\lambda}{\int_{300\,nm}^{320\,nm} I(\lambda) \cdot w(\lambda) d\lambda}$$

$PF_B$ is defined as:

$$PF_B = 1 - \frac{\int_{280\,nm}^{300\,nm} I(\lambda) \cdot w(\lambda) \cdot T(\lambda) d\lambda}{\int_{280\,nm}^{300\,nm} I(\lambda) \cdot w(\lambda) d\lambda}$$

the topical composition blocks a percentage $PF_C$ of radiation in wavelength range C (320 to 340 nm) that is greater than $PF_A$, wherein $PF_C$ is defined as:

$$PF_C = 1 - \frac{\int_{320\,nm}^{340\,nm} I(\lambda) \cdot w(\lambda) \cdot T(\lambda) d\lambda}{\int_{320\,nm}^{340\,nm} I(\lambda) \cdot w(\lambda) d\lambda}$$

$PF_C - PF_A$ is at least about 5%; and $\lambda$ is a wavelength of radiation, $I(\lambda)$ is an intensity of radiation according to solar irradiance standard ASTM G177-03 passing through the topical composition at a given wavelength in W/m²/nm, $T(\lambda)$ is the mean transmittance of a topical composition determined using the methodology outline in the US FDA Broad Spectrum Test (21 CFR 201.327 (j), Jul. 5, 2011), and $w(\lambda)$ is a weighting function defined as:

$$w(\lambda) = \begin{cases} 1 & 280\,nm < \lambda \le 298\,nm \\ 10^{0.094(298-\lambda)} & 298\,nm < \lambda \le 320\,nm \end{cases}$$

$PF_B - PF_A$ is at least about 10%; and further wherein the first compound and the second compound are present in amounts and in a ratio such that the topical composition has an absorbance spectra forming a spectra valley defined by a wavelength range from 306 nm to 315 nm, the spectra valley allowing passage of light to generate the erythemally weighted irradiance therapeutic response, wherein the topical composition comprises 4% hesperidin by weight percent and 1.125% or 2.5% diethylamino hydroxybenzoyl hexyl benzoate by weight percent.

2. The method of claim 1, wherein $PF_B - PF_A$ is at least about 25%.

3. The method of claim 2, wherein $PF_B - PF_A$ is at least about 50%.

4. The method of claim 1, wherein $PF_C - PF_A$ is at least about 10%.

5. The method of claim 4, wherein $PF_C - PF_A$ is at least about 15%.

6. The method of claim 1, wherein the spectra valley allows for maximum transmittance of erythemally weighted EMR having a wavelength of 311 nm within a wavelength range from 280 to 320 nm.

7. A method of treating a human suffering from a skin disorder to produce a therapeutic response in the human patient by delivering, from ambient solar radiation, a dose of EMR within at least a predetermined wavelength band greater than about 300 nm to the skin of a human subject, comprising the steps of:

covering a region of the skin with a topical composition comprising:

a cosmetic-grade carrier suitable for application to the human skin;

a first compound, suitable for application to human skin, which blocks more total radiation within wavelength range B (280 to 300 nm) than it blocks in wavelength range A (300 to 320 nm); and a second compound, suitable for application to human skin, which blocks more total radiation within wavelength range C (320 to 340 nm) than it blocks in wavelength range A wherein the topical composition blocks a percentage $PF_B$ of radiation in wavelength range B that is greater than a percentage $PF_A$ of radiation blocked in wavelength range A, $PF_A$ is defined as:

$$PF_A = 1 - \frac{\int_{300\,nm}^{320\,nm} I(\lambda) \cdot w(\lambda) \cdot T(\lambda) d\lambda}{\int_{300\,nm}^{320\,nm} I(\lambda) \cdot w(\lambda) d\lambda}$$

$PF_B$ is defined as:

$$PF_B = 1 - \frac{\int_{280\,nm}^{300\,nm} I(\lambda) \cdot w(\lambda) \cdot T(\lambda) d\lambda}{\int_{280\,nm}^{300\,nm} I(\lambda) \cdot w(\lambda) d\lambda}$$

the topical composition blocks a percentage $PF_C$ of radiation in wavelength range C (320 to 340 nm) that is greater than $PF_A$, wherein $PF_C$ is defined as:

$$PF_C = 1 - \frac{\int_{320\,nm}^{340\,nm} I(\lambda) \cdot w(\lambda) \cdot T(\lambda) d\lambda}{\int_{320\,nm}^{340\,nm} I(\lambda) \cdot w(\lambda) d\lambda}$$

$PF_C - PF_A$ is at least about 5%; and $\lambda$ is a wavelength of radiation, $I(\lambda)$ is an intensity of radiation according to solar irradiance standard ASTM G177-03 passing through the topical composition at a given wavelength in W/m²/nm, $T(\lambda)$ is the mean transmittance of a topical composition determined using the methodology online in the US FDA Broad Spectrum Test (21 CFR 201.327 (j), Jul. 5, 2011), and w(λ) is a weighting function defined as:

$$w(\lambda) = \begin{cases} 1 & 280 \text{ nm} < \lambda \leq 298 \text{ nm} \\ 10^{0.094(298-\lambda)} & 298 \text{ nm} < \lambda \leq 320 \text{ nm} \end{cases}$$

$PF_B - PF_A$ is at least about 10%; and
wherein the first compound and the second compound are present in amounts and in a ratio such that the topical composition has an absorbance spectrum forming a spectrum valley defined by a wavelength range from 306 nm to 315 nm, the spectrum valley allowing passage of light to generate the erythemally weighted irradiance therapeutic response, wherein the topical composition comprises 4% hesperidin by weight percent and 1.125% or 2.5% diethylamino hydroxybenzoyl hexyl benzoate by weight percent;

exposing the person to the ambient solar radiation;
making a dosage calculation by executing a dosage calculator application program which has been stored in a general purpose digital computer's memory, to impart dosage calculation functionality to the general purpose digital computer by changing the state of the computer's arithmetic logic unit when a set of program instructions of the dosage calculator application program are executed, wherein the program instructions comprise the following steps:
  obtaining (A) actual or predictive solar radiation data for a place in which the subject is located and a time during which the exposure is occurring or is to occur;
  obtaining (B) a number or set of numbers representing the UV transmission characteristics of the topical composition within the predetermined wavelength band; and
  calculating, based on a set of available data which includes (A) and (B), a predetermined period of time reflecting a therapeutically effective amount of exposure time to the ambient solar radiation for treatment of a condition of the human subject in need of therapeutic treatment by exposure to UV light; and
stopping the exposure of the person to the ambient solar radiation after the passage of the predetermined period of time.

8. The method of claim 7, wherein the skin disorder is selected from the group consisting of psoriasis, vitiligo, acne, atopic dermatitis, and pruritis.

9. A method of treating a human patient suffering from psoriasis, vitiligo, atopic dermatitis, and/or pruritis, comprising:
  delivering, from ambient solar radiation, a dose of EMR to skin of a human subject by:
    covering a region of the skin with a topical composition;
    exposing the human subject to the ambient solar radiation for a predetermined period of time to generate an erythemally weighted irradiance therapeutic response; and
    stopping the exposure of the human subject to the ambient solar radiation after the passage of the predetermined period of time;
  wherein the topical composition comprises:
    a cosmetic-grade carrier suitable for application to the human skin;
    a first compound, suitable for application to human skin, which blocks more total radiation within wavelength range B (280 to 300 nm) than it blocks in wavelength range A (300 to 320 nm); and
    a second compound, suitable for application to human skin, which blocks more total radiation within wavelength range C (320 to 340 nm) than it blocks in wavelength range A
  wherein:
    the topical composition blocks a percentage $PF_B$ of radiation in wavelength range B that is greater than a percentage $PF_A$ of radiation blocked in wavelength range A,
    $PF_A$ is defined as:

$$PF_A = 1 - \frac{\int_{300\,nm}^{320\,nm} I(\lambda) \cdot w(\lambda) \cdot T(\lambda) d\lambda}{\int_{300\,nm}^{320\,nm} I(\lambda) \cdot w(\lambda) d\lambda}$$

$PF_B$ is defined as:

$$PF_B = 1 - \frac{\int_{280\,nm}^{300\,nm} I(\lambda) \cdot w(\lambda) \cdot T(\lambda) d\lambda}{\int_{280\,nm}^{300\,nm} I(\lambda) \cdot w(\lambda) d\lambda}$$

the topical composition blocks a percentage $PF_C$ of radiation in wavelength range C (320 to 340 nm) that is greater than $PF_A$, wherein $PF_C$ is defined as:

$$PF_C = 1 - \frac{\int_{320\,nm}^{340\,nm} I(\lambda) \cdot w(\lambda) \cdot T(\lambda) d\lambda}{\int_{320\,nm}^{340\,nm} I(\lambda) \cdot w(\lambda) d\lambda}$$

$PF_C - PF_A$ is at least about 5%; and
λ is a wavelength of radiation, I(λ) is an intensity of radiation according to solar irradiance standard ASTM G177-03 passing through the topical composition at a given wavelength in W/m²/nm, T(λ) is the mean transmittance of a topical composition determined using the methodology outline in the US FDA Broad Spectrum Test (21 CFR 201.327 (j), Jul. 5, 2011), and w(λ) is a weighting function defined as:

$$w(\lambda) = \begin{cases} 1 & 280 \text{ nm} < \lambda \leq 298 \text{ nm} \\ 10^{0.094(298-\lambda)} & 298 \text{ nm} < \lambda \leq 320 \text{ nm} \end{cases}$$

$PF_B - PF_A$ is at least about 10%; and
further wherein the first compound and the second compound are present in amounts and in a ratio such that the topical composition has an absorbance spectra forming a spectra valley defined by a wavelength range from 306 nm to 315 nm, the spectra valley allowing passage of light to generate the erythemally weighted irradiance therapeutic response,
further wherein the first compound consists of silymarin and the second compound consists of diethylamino hydroxybenzoyl hexyl benzoate in a weight to weight ratio within a range from 1:2 to 5:6.

10. The method of claim 9, wherein $PF_B - PF_A$ is at least about 25%.

11. The method of claim 10, wherein $PF_B - PF_A$ is at least about 50%.

12. The method of claim 9, wherein $PF_C - PF_A$ is at least about 10%.

13. The method of claim 12, wherein $PF_C - PF_A$ is at least about 15%.

14. The method of claim 9, wherein the spectra valley allows for maximum transmittance of erythemally weighted EMR having a wavelength of 311 nm within a wavelength range from 280 to 320 nm.

* * * * *